US012734355B2

(12) United States Patent
Ionescu

(10) Patent No.: US 12,734,355 B2
(45) Date of Patent: Sep. 15, 2026

(54) DEVICE FOR CARDIAC ELECTROPHYSIOLOGY PROCEDURE

(71) Applicant: Bogdan Gabriel Ionescu, Cologne (DE)

(72) Inventor: Bogdan Gabriel Ionescu, Cologne (DE)

( * ) Notice: Subject to any disclaimer, the term of this patent is extended or adjusted under 35 U.S.C. 154(b) by 877 days.

(21) Appl. No.: 17/611,913

(22) PCT Filed: May 29, 2020

(86) PCT No.: PCT/IB2020/055111

§ 371 (c)(1),
(2) Date: Jan. 6, 2023

(87) PCT Pub. No.: WO2020/250074

PCT Pub. Date: Dec. 17, 2020

(65) Prior Publication Data

US 2023/0329616 A1 Oct. 19, 2023

(30) Foreign Application Priority Data

Jun. 13, 2019 (EP) .................................... 19180033
Dec. 23, 2019 (WO) ................. PCT/EP2019/086922

(51) Int. Cl.
*A61N 1/05* (2006.01)
*A61B 5/00* (2006.01)
(Continued)

(52) U.S. Cl.
CPC ............ *A61N 1/0565* (2013.01); *A61B 5/287* (2021.01); *A61B 5/304* (2021.01); *A61B 5/308* (2021.01);
(Continued)

(58) Field of Classification Search
CPC .......... A61B 2018/00827; A61B 2018/00767; A61B 2018/00875; A61B 2018/165;
(Continued)

(56) References Cited

U.S. PATENT DOCUMENTS 3,580,240 A 5/1971 Cosentino
5,357,956 A 10/1994 Nardella
(Continued)

FOREIGN PATENT DOCUMENTS

DE 102018133630.6 12/2018
EP 1487366 A2 12/2007
(Continued)

OTHER PUBLICATIONS

Extended European Search Report in European Application No. 19180033.3, mailed on Oct. 23, 2019, 6 pages.
(Continued)

*Primary Examiner* — Eun Hwa Kim
(74) *Attorney, Agent, or Firm* — Fish & Richardson P.C.

(57) ABSTRACT

A cardiac electrophysiology device part of a catheter device or of a cardiac implantable device comprising a plurality of electrodes which are connected via a selector switch over a resistor to a neutral electrode. Voltage and current at one of the electrodes are measured to set the site and the timing of channelling current out from the heart optionally by the electrophysiology therapy.

12 Claims, 4 Drawing Sheets

(51) Int. Cl.

| | |
|---|---|
| ***A61B 5/287*** | (2021.01) |
| ***A61B 5/304*** | (2021.01) |
| ***A61B 5/308*** | (2021.01) |
| ***A61B 5/318*** | (2021.01) |
| ***A61B 5/367*** | (2021.01) |
| ***A61N 1/362*** | (2006.01) |
| ***A61N 1/372*** | (2006.01) |

(52) U.S. Cl.
CPC .............. *A61B 5/318* (2021.01); *A61B 5/367* (2021.01); *A61B 5/6857* (2013.01); *A61B 5/6858* (2013.01); *A61N 1/057* (2013.01); *A61N 1/362* (2013.01); *A61N 1/37223* (2013.01); *A61N 2001/058* (2013.01)

(58) Field of Classification Search
CPC ... A61B 2018/167; A61B 18/16; A61B 5/287; A61B 5/367; A61B 5/6857; A61B 5/6858; A61B 5/204; A61B 5/361; A61B 5/363; A61B 5/318; A61B 5/6852
See application file for complete search history.

(56) References Cited

U.S. PATENT DOCUMENTS

| | | | | |
|---|---|---|---|---|
| 5,447,529 | A | 9/1995 | Marchlinkski et al. | |
| 6,615,073 | B1 | 9/2003 | Panescu et al. | |
| 7,879,029 | B2 | 2/2011 | Jimenez | |
| 8,502,364 | B2 | 8/2013 | Kato et al. | |
| 2001/0039413 | A1 | 11/2001 | Bowe | |
| 2005/0177053 | A1 | 8/2005 | Boveja et al. | |
| 2008/0091135 | A1 | 4/2008 | Draghia-Akli et al. | |
| 2009/0062876 | A1 | 3/2009 | Cohen et al. | |
| 2009/0281539 | A1* | 11/2009 | Selig | A61B 18/16 606/41 |
| 2011/0245888 | A1 | 10/2011 | Badelt et al. | |
| 2012/0221001 | A1 | 8/2012 | Tegg et al. | |
| 2013/0189823 | A1 | 7/2013 | Kamath et al. | |
| 2015/0119671 | A1* | 4/2015 | Varma | A61B 5/6853 600/374 |
| 2018/0168729 | A1 | 6/2018 | Pratten et al. | |
| 2018/0221085 | A1 | 8/2018 | Blanck et al. | |
| 2019/0214547 | A1 | 7/2019 | Onoda et al. | |
| 2022/0347466 | A1 | 11/2022 | Ionescu | |
| 2023/0086060 | A1 | 3/2023 | Ionescu | |

FOREIGN PATENT DOCUMENTS

| | | | | |
|---|---|---|---|---|
| EP | 2095784 A1 | 9/2009 | | |
| EP | 1233716 B1 | 7/2014 | | |
| EP | 19180033.3 | 6/2019 | | |
| EP | 3673846 A1 | 7/2020 | | |
| GB | 2278548 A * | 12/1994 | A61B 18/1487 | |
| JP | 2007-185505 A | 7/2007 | | |
| JP | 5880512 B2 | 3/2016 | | |
| WO | WO-03089997 A2 * | 10/2003 | A61B 5/6858 | |
| WO | WO 2007/047681 A2 | 4/2007 | | |
| WO | WO 2011/084450 A1 | 7/2011 | | |
| WO | WO-2015148541 A1 * | 10/2015 | A61M 31/00 | |
| WO | PCT/EP2019/086922 | 12/2019 | | |
| WO | WO 2021/053659 A1 | 3/2021 | | |
| WO | WO 2021/240486 A1 | 12/2021 | | |

OTHER PUBLICATIONS

International Preliminary Report on Patentability in International Application No. PCT/EP2019/086922, mailed on Jul. 8, 2021, 8 pages.

International Preliminary Report on Patentability in International Application No. PCT/IB2020/055111, mailed on Dec. 23, 2021, 10 pages.

International Preliminary Report on Patentability in International Application No. PCT/IB2020/062261, mailed on Jul. 2, 2022, 10 pages.

International Preliminary Report on Patentability in International Application No. PCT/IB2021/054984, mailed on Dec. 8, 2022, 8 pages.

International Search Report and Written Opinion in International Application No. PCT/EP2019/086922, mailed on Apr. 14, 2020, 10 pages.

International Search Report and Written Opinion in International Application No. PCT/IB2020/055111, mailed on Sep. 8, 2020, 14 pages.

International Search Report and Written Opinion in International Application No. PCT/IB2020/062261, mailed on Feb. 18, 2021, 14 pages.

International Search Report and Written Opinion in International Application No. PCT/IB2021/054984, mailed on Sep. 13, 2021, 12 pages.

* cited by examiner 120
121
122
123
124
125
131
150
155
151
156
160
170

I
non-NDR
4
NDR
3
non-NDR
S
1
NDR
non-NDR
non-NDR
N
2
V

I
NDR
NDR
NDR
NDR
S
SN
N
V
Fig.4.1

DEVICE FOR CARDIAC ELECTROPHYSIOLOGY PROCEDURE

CROSS-REFERENCE TO RELATED APPLICATIONS

This application claims the priority of EP19180033.3, filed on Jun. 13, 2019 and PCT/EP2019/086922 filed on Dec. 23, 2019, which claim priority to DE102018133630.6 filed on Dec. 27, 2018. The entire disclosures of the above applications are incorporated herein by reference.

FIELD OF THE INVENTION

The present invention provides methods for performing cardiac mapping procedures to provide the cardiac electrophysiology therapy (EPT); electrophysiology catheters, cardiac implantable devices and cardiac implantable leads.

BACKGROUND

EP 1233716 B1 discloses a catheter which has a helical electrode member. The effective length and diameter of this electrode member can be adjusted by actuating a stylet which runs through a hollow, flexible body of the catheter. The stylet runs through hollow, flexible body before exiting the body at aperture. The stylet re-enters the body of the catheter through aperture and in to anchor member.

US 2001/0039413 A1 describes a steerable catheter. The catheter comprises a wire housed within a sheath which is formed of a shape-retentive and resilient material having a curved shape at its distal end. An operator can adjust the shape and radius of curvature of the distal end region.

US 2005/0177053 A1 shows as system for perform an ablation procedure. The handle shown in the system has a safety switch for shutting down the RF generator which delivers current to the heart via the catheter.

WO 03/089997 A2 discloses a method and apparatus for control of ablation energy in an electrophysiology catheter. It does not provide means for selective stimulation of the heart. It uses resistors to form a virtual electrical null point (average) for unipolar electrogram channels. The resistors are fixedly connected and cannot be switched.

U.S. Pat. No. 5,357,956 A discloses an apparatus for monitoring an endocardial signal during ablation with the same single electrode. A switch switches either the ablation device or the monitor to the single electrode.

DE102018133630.6, EP19180033.3 and PCT/EP2019/086922 disclose a cardiac electrostimulation device, specially configured to channel current out from the heart via a resistor connected to a switch during an electrophysiology procedure which involves cardiac ablation.

JP588051282 discloses a method of forming a semiconductor device member forming liquid, semiconductor device member, and semiconductor light emitting device. According to the JP5880512B2 the liquid semiconductor is not suitable for use in a biological environment.

US20130189823A1relates to electrically active devices (e.g., capacitors, transistors, diodes, floating gate memory cells, etc.) having dielectric, conductor, and/or semiconductor thin layers with smooth and/or dome-shaped profiles and methods of forming such devices by depositing or printing (e.g., inkjet printing) an ink composition that includes a semiconductor, metal, or dielectric precursor.

SUMMARY OF THE INVENTION

The modern era of cardiac electrophysiology started in 1986 with the radio frequency ablation. Different forms of energy like cryoablation, laser, ultrasounds, have been added since then, all of them are world wide in use nowadays.

So far, the ablation is the only ways to treat a cardiac arrhythmia by further scarring the already damaged arrhythmogenic tissue known as arrhythmic substrate, in an intent to stop the arrhythmia and/or render it non reproducible (the patent literature cited above under the description of the related art represents merely a selection).

The ablation procedures not exempted from serious complications due to their aggressive nature, typically involving destruction of the heart tissue, are far from being effective specially in patients with common arrhythmias such as atrial fibrillation, atrial tachycardias and ventricular arrhythmias as depicted by the high rate of recurrences and even redo procedures in most EP-labs around the world.

Exceeding the prior art by far, the invention opens a not yet explored realm of cardiac electronics. The invention discloses a method that provides for the first time the electronic mechanisms of an arrhythmia induction, maintenance and termination at intimate-cellular level at the arrhythmic substrate, that restores the electronic properties of the arrhythmic substrate by channeling current out from the substrate, by inking it in or both, in an intent to stop an arrhythmia and render it non reproducible; a cardiac electrophysiology device and a versatile catheter device for the electrophysiology therapy. The innovative method involves cardiac mapping and electronic cardiac mapping of the arrhythmic substrate. The innovative method involves three dimensional cardiac mapping.

The solution of the problem is described in the independent claims. The dependent claims relate to further improvements of the invention.

BRIEF DESCRIPTION OF THE DRAWINGS

In the following, the invention will be described by way of example, without limitation of the general inventive concept, on examples of embodiment with reference to the drawings.

FIG. 3 shows a sectional view of the heart with a catheter.

FIG. 4.1 depicts the co-existence of more than one NOR domains in more that one voltage or current ranges available to the arrhythmic substrate.

DETAILED DESCRIPTION

Figure 1:
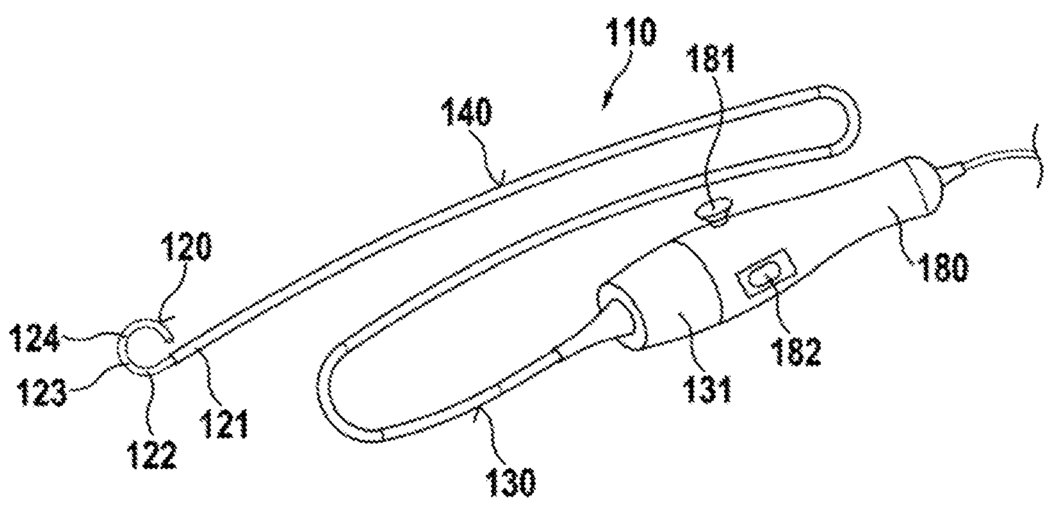
FIG. 1 shows a catheter device.

The Human Heart is a Very Complex Organ, which Exerts Efficient and Synchronized Muscle Contractions when the Electrical Current Flows Properly Throughout it.

To provide a normal heartbeat, a current flow path is set from the sinoatrial node down to the atrioventricular node and then throughout the ventricles along the specific His-Purkinje system when a naturally occurring voltage applies to the heart. The atria contract first, followed by the ventricles. This is essential for the proper functioning of the heart. The sequence of these electric events along this current path is called heart depolarization. The heart depolarization is commonly followed by the heart repolarization. Despite the fact that the repolarization was widely depicted, there is no clear evidence to which current path is it associated, in other words how does the current exit the heart before, or keep traveling throughout it to the next depolarization. The atrial repolarization has a tiny expression on the surface ECG so far not yet properly characterized.

Contrary, the ventricular repolarization has a robust surface ECG expression, known as the terminal phase. To date, there is no consistent data that can derived from prior art to sustain that the terminal phase actually electromagnetically supports the next depolarization. An existing anatomical model of the heart, the so-called myocardial band may allow a novel theory according to which repolarization can electromagnetically induce the atrioventricular node to set the current path required to the next depolarization-repolarization sequence, commonly electrophysiologically depicted by the H-V potentials recorded with a catheter suitable placed into a beating heart. The phenomenon typically related to the presence of an induction coil in physics, has never been related to the anatomy, nor to the twisting mechanical performance of a beating heart until now. The theory according to which the repolarization electromagnetically reloads the heart to allow at least in part the next depolarization is new over the prior art, is not confined to this invention and may be further on explained in separate embodiments.

When a natural occurring voltage applies to the heart in vivo, a resultant improper or impaired flow of the electrical current throughout the heart disrupts the heart's proper function and causes or represents a cardiac arrhythmia. Arrhythmias can present as the electrical current enters the heart from another regions to initiate and maintain abnormal rhythms, what is called an ectopic or focal arrhythmia. Another possibility is, when current circulates repetitively in a closed circuit involving various amounts of heart regions, what is called a reentrant arrhythmia. In both situations, that heart region responsible for the initiation and/or maintenance or the arrhythmia defines the arrhythmic substrate. The arrhythmias are paroxysmal, incessant, persistent or long lasting persistent and permanent.

In the cardiac electrophysiology, it has become state of the art that the signals associated with an arrhythmia have lower amplitude when compared to the normal signals not associated with an arrhythmia, that they generally anticipate or follow the normal signals, such as in case of the so called late potentials, and that they typically exhibit a fragmentation pattern and/or a longer duration in comparison with the normal signals not associated with an arrhythmia. An explanation of this phenomenon has not yet been provided. It is the scope of the invention to state that the genesis of such signals at the level of the arrhythmic substrate (near field signals) or remote from it (far field signals) is truly explained by the electronic behavior of the arrhythmic substrate.

Furthermore, it is not the scope of the invention to provide a detailed analysis of the cardiac signals associated with an arrhythmia as they are a surrogate or the result of the electronic behavior of the arrhythmic substrate and not the cause of it.

Figure 4:
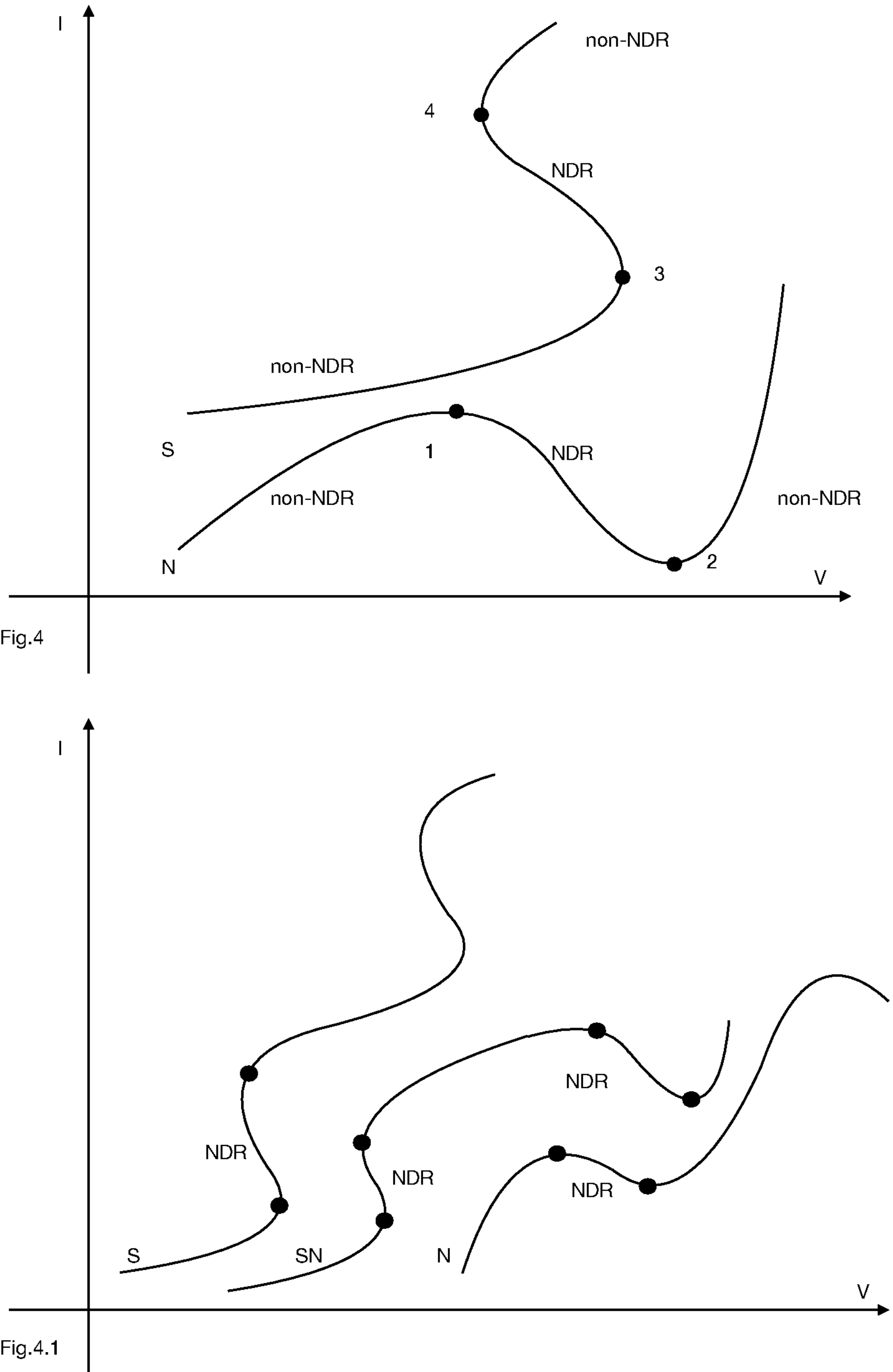
FIG. 4 shows the VI (voltage-current} electronic distribution at the level of the arrhythmic substrate.

The invention postulates that an arrhythmia occurs whenever the variation of the voltage (V) and the variation of the current (I) have opposite signs at the level of the arrhythmic substrate, id.est. whenever the arrhythmic substrate exhibits negative differential resistance (NOR). In other words, according to the invention, the arrhythmia occurs whenever the VI relationship at the level of the arrhythmic substrate is confined to at least one NOR domain (such as 1-2 domains at the N curve or 3-4 domains at the S curve), as depicted in FIG. 4 and FIG. 4.1. An arrhythmia occurs whenever the arrhythmic substrate at a given voltage or current exhibits a NOR behavior and resumes whenever the NOR at the level of the arrhythmic substrate is reset to a non-NOR behavior by altering the value of the voltage, or current or both that apply. The co-existence of more than one NOR domains in more than one voltage or current ranges available to the arrhythmic substrate, as depicted in FIG. 4.1 relies on the complexity and on the operating mode of the arrhythmic substrate that provides a polymorphic presentation of an arrhythmia. Typically, an increasing voltage that applies to the substrate triggers an arrhythmia at point 1 or 3, and terminates a given arrhythmia at point 2 and respectively 3 and, vice versa, a decreasing voltage applying to the substrate, triggers an arrhythmia at point 2 or 4 and further on terminates the given arrhythmia at point 1 or 4. Further on, the invention considers that the leftwards slippage of the arrhythmic substrate VI relationship over the NOR domain during an arrhythmia may be a spontaneous phenomenon occurring during an arrhythmia at the level of the arrhythmic substrate which is responsible for a spontaneous interruption of an arrhythmia at point 1 or 4. This occurs by a progressive extinction of the voltage that caused that arrhythmia up to point 1 or 4 and/or by primarily increasing current within the arrhythmic substrate according to the excitability of the substrate during an arrhythmia up to point 1 or 4 where interruption is achieved. By the contrary, an active interruption of an arrhythmia, as achieved with interventional maneuvers implies the rightwards slippage of an arrhythmia over the NOR domain up to the local minimum current value at point 2 or 3 where interruption occurs. The active interruption according to the invention implies both increasing voltage and/or decreasing current during an arrhythmia at the level of the arrhythmic substrate. This further on may imply only channeling current out from the substrate to primarily diminish current within the substrate as a single therapeutic option or both as achieved, according to the invention by the electrophysiology therapy (EPT) at the level the arrhythmic substrate in an intent to prevent that the arrhythmic substrate can exhibit a NOR-like behavior again. The electrophysiology therapy EPT is herein proposed to restore the electronic properties of the arrhythmic substrate responsible for the mechanism of the arrhythmia.

To study the mechanism of an arrhythmia in the EP-lab, pharmaceutical manipulation is used and/or electrical stimuli are typically applied from an external voltage source, called stimulator, via catheters suitable positioned within the heart, typically in contact to the arrhythmic substrate.

These maneuvers establish new current paths inside the heart that create a mismatch between the voltage and the current within the arrhythmic substrate thus allowing induction, maintenance of an arrhythmia as well as the termination of the arrhythmia as the mismatch ceases. The invention considers that the mismatch implies that voltage and current vary in opposite directions within the arrhythmic substrate resulting in a negative value of the instantaneous differential resistance recorded topically at the level of the arrhythmic substrate by mapping the substrate.

Common pharmacologic and/or stimulation maneuvers may reveal phenomena such as jump, Wenckebach, entrainment and overdrive at the level of the arrhythmic substrate, all of these features already known in the prior art, but so far not yet intimately explained as in the light of the electronic properties of the arrhythmic substrate. The mismatch induced in the EP-lab is deemed further on to simulate a natural occurring condition that involves the induction and the maintenance of an arrhythmia. According to the degree of the mismatch induced, a variable amount of the arrhythmic substrate may be revealed; usually in the EP-lab and by using common pharmacologic and/or electric stimulation maneuvers, one may not want to reveal an arrhythmic substrate that exceeds the extent of the arrhythmic substrate related to the clinical arrhythmia. However, the arrhythmic substrate may be sometimes defined and treated in the absence of the arrhythmia itself, given that the heart recognizes a hysteresis-like electrophysiology behavior, responsible for sequences of spontaneous initiation, maintenance and even termination of an arrhythmia after an arrhythmia-free time interval or remote from previous arrhythmias.

A first embodiment of the invention relates to a cardiac electrophysiology device and a catheter device adapted for direct tissue electromechanical coupling.

The cardiac electrophysiology device may comprise an active electrode device comprising at least one or at least two active electrodes, a neutral electrode, a resistor connected to the neutral electrode and a second selector switch configured to connect the resistor further to at least one of the active electrodes. According to the setting of the second selector switch (155), a selected active electrode may be connected via the resistor (151) to the neutral electrode (170), forming an electrical current path from the selected active electrode to the patient body. It may further comprise a first selector switch configured to connect a sensor device comprising a voltage (161) and current (162) meters to at least one of the active electrodes. The selector switches may be implemented but not only as semiconductor circuits. The sensor device (160) derives the instantaneous differential resistance from the values provided from 161 and 162 and provides real time output data particularly when the measured value of the instantaneous differential resistance is or turns negative, or is or turns equal or greater than zero during the cardiac mapping. The neutral electrode may be connected to the at least one resistor or the sensor device directly or via at least one selector switch which may be part of the control unit and may be configured to be attached to a patient. The neutral electrode closes the electrical circuit via the at least one electrode from the electrode device. The purpose and the architecture of the electrophysiology device and its connections are unique. For attaching the electrode to a patient, the neutral electrode may have an adhesive surface.

The cardiac mapping, further on referred herein as mapping, typically involves moving of a mapping catheter inside the heart or over the external surface of the heart in electromechanical coupling with the heart tissue by mapping maneuvers executed from the operating physician directly with his hands over the catheter device (110) that comprises a mapping catheter according to the invention, or indirectly, remote, by commanding a computer connected to a robotic mapping system further on connected to the catheter device (110). Typically, mapping results in a map of a cardiac structure, commonly a three dimensional anatomical map of said cardiac structure typically involving the arrhythmic substrate. The mapping catheter assures the abiotic/biotic interface between the catheter device and the heart. In other embodiments, a mapping catheter localization system may be provided.

At various points in the heart, a cardiac electrogram (EGM) may be recorded. During the measurement, the dissipation of electrical signals within the heart may be estimated with the aforementioned catheter device.

A control unit (150) may be configured to control the first selector switch (156) and the second selector switch (155) during mapping.

By setting the value of the variable resistor, current can be set up to be channeled out from the heart via at least one electrode at the distal end of the catheter device. The amended current dissipation can be recorded via the sensor device 160 and may be configured to be maximal depending upon the setting of the value of the resistor (either a very low or a very high setting within, but not limited to the proposed ranges, from 0.10 ohm to 2 mega ohm). In whichever case and provided that the first selector and the second selector switch refer to the same selected electrode, the sensor device 160 may be said to work in an unipolar mode. Again, in whichever case and provided that the first and the second selector switch refer to different selected electrodes, the sensor device 160 may be said to work in a bipolar mode. Preferably, the value of the resistor is set high for the bipolar mode, or optionally low for the unipolar mode.

It is possible then, provided the unipolar setting mode of the sensor device to unipolar point by point mapping of the totality of points that form the arrhythmic substrate.

It is possible then, provided the bipolar setting mode of the sensor device to bipolar point by point mapping of the totality of points that form the arrhythmic substrate. Further on, and according to the method disclosed herein in claim 3, it is possible then, by repetitively applying the said method disclosed herein in said claim 3 for each point of the arrhythmic substrate, to map the totality of points that form the arrhythmic substrate to further on provide the electrophysiology therapy to all of them according to the method disclosed further on herein, in claims 4-9.

As aforementioned, the heart exhibits a measurable spontaneous electrical current flow when a voltage applies, that respects a hysteresis behavior over time.

The invention postulates that, in normal conditions the normal spontaneous electrical activity of the heart prevents the existence of regions within the heart in which a measurable negative differential resistance can be derived and demonstrated by mapping.

Further on, the invention postulates that the spontaneous electrical activity of the heart is altered in case of the existence or coexistence of regions confined to the heart in which the presence of a measurable negative differential resistance (NDR) can be demonstrated by mapping. The alteration may involve a predisposition to develop an arrhythmia, the arrhythmia itself either self-limited or persistent, a combination of arrhythmias either self-limited or persistent, as well as a complete loss of the spontaneous electrical activity of the heart. Any of these alterations or a combination of them may be reversed by identifying and treating the regions found to have a measurable negative differential resistance (NDR) at mapping, for which the methods and devices disclosed herein in this invention may constitute one first option. The implementation of the nano technologies, the use of now trendy materials such as soluble graphene or bio derivates, but not only, may optimize both the accuracy of the methods and the spatial resolution of the devices disclosed further on, herein.

When the value of the differential resistance measured by the sensor device (160) is or turns negative, and according to the setting of the first selector switch (156), the selective active electrode connected to the first switch (156) may be considered to be approaching the arrhythmic substrate or in electromechanical coupling with the arrhythmic substrate that should be targeted for the electrophysiology therapy (EPT). A floating selective active electrode connected to the first switch (156), provided according to the three dimensional architecture of the mapping catheter during mapping cannot provide a negative value of the measured differential resistance to the sensor device 160; therefore the selected active electrode providing the sensor device 160 with a negative differential resistance value has to be in electromechanical coupling with the arrhythmic substrate and cannot be a floating electrode.

According to the present disclosure the electrophysiology therapy (EPT) implies the ink staining of the arrhythmic substrate, with the electronic ink as disclosed further on, herein below.

Staining inks are tailored in such a way that they are able to resist the immune response, the accidental or not desired blood clotting and viral and/or bacterial colonization.

The selective active electrode in electromechanical coupling with the arrhythmic substrate may further on be set by mapping maneuvers and by correspondingly changing the setting of the first selector switch (156), to be the electrode most suitable, according to the three dimensional architecture of the mapping catheter, for the electrophysiology therapy (EPT}, preferably, but not limited to one of the tip or central electrodes of the mapping catheter. When the mapping maneuvers are not sufficient to optimally position the electrode most suitable, according to the three dimensional architecture of the mapping catheter for the electrophysiology therapy, in electromechanical coupling to the arrhythmic substrate, or due to slippage of the mapping catheter at the abiotic/biotic interface, an additional mapping catheter, preferably with another architecture may be optionally employed and suitable positioned directly in electromechanical coupling to the arrhythmic substrate, as previously identified and according to the initial position of the first mapping catheter and the initial setting of the first selection switch (156), to further on be used only for the electrophysiology therapy (EPT). Given the multipolar design of most modern mapping catheters (linear, circular, basket, grid, mesh, orthogonal close unipolar or balloon}, a second mapping catheter is usually not needed.

In the usual case that the second mapping catheter is not needed and provided that the setting of the catheter device achieved by mapping maneuvers did not change by additional mapping maneuvers or movements of the mapping catheter and that the setting of the selective active electrode connected with the first selector switch (156) did also not change after the first mapping maneuvers, so that the selective active electrode most suitable according to the three dimensional architecture of the mapping catheter for the electrophysiology therapy is still in electromechanical coupling to the arrhythmic substrate, the electrophysiology therapy (EPT) is provided to the arrhythmic substrate. In the other case when a second mapping catheter is needed, it is used only for directly providing the electrophysiology therapy to the arrhythmic substrate, previously established with the first mapping catheter during mapping.

Most mapping catheters are open irrigated catheters allowing fluid passage from their proximal end to their distal end through their internal lumen, which prevents fluid leakages and is configured to have a proximal and a distal orifice. The proximal orifice is connected via the catheter device with a fluid reservoir, optionally controlled by a mechanical pump which establishes the exact amount of flow to be passed that may further on be set according to the clinical settings of the patient, the type of the arrhythmia and the type of the mapping catheter as well. The distal orifice opens externally when the mapping catheter is not inserted into the body, internally into another body structure before mapping or within the heart or adjacent to the external surface of the heart during mapping.

In the prior art, mapping catheters are commonly flushed with sterile saline, optionally heparinized sterile saline to prevent clot adhesion to the distal end during mapping.

Exceeding by far the prior art, the invention discloses the electrophysiology therapy (EPT) which comprises the passage of a potentiometric or an organic semiconductor staining ink through the lumen of the mapping catheter, the delivery of said staining ink to the arrhythmic substrate and the ink staining of the arrhythmic substrate. The invention postulates that the electrophysiology therapy (EPT) induces a minimal, rather beneficial reduction of the shear and/or stretch stress at the level of the arrhythmic substrate where it applies.

To provide conformity with the arrhythmic substrate, the staining ink may be chosen further on to be lipophilic, oxidized lipophilic or polymeric or to non-invasively dissolve into the arrhythmic substrate.

To provide conformity with the arrhythmic substrate, the staining ink may be chosen further on to exhibit magnetic properties. An external magnetic field may be configured to be provided and tailored to provide the electrophysiology therapy (EPT) at the level of the arrhythmic substrate. In the prior art, the magnetic navigation of a magnetic guidable catheter in a magnetic environment applied to a human body as provided by a magnetic navigation system is commonly referred as the navigation of a "small magnetic body". Exceeding by far the prior art, the invention considers that the electrophysiology therapy (EPT) implies the navigation of the innovative staining ink, that represents a liquid "small magnetic body" in close proximity to the arrhythmic substrate in said tailored magnetic environment applied to a human body. This provides the electrophysiology therapy (EPT) in close proximity to the arrhythmic substrate. This further on provides the electrophysiology therapy (EPT) conformal to said arrhythmic substrate. In other embodiments, a dedicated catheter device containing a small magnetic body and magnetically guidable in said magnetic field independently from the magnetic exhibiting properties staining ink, the liquid small magnetic body is provided and configured for the electrophysiology therapy (EPT). It is obvious for those skilled in the art that the navigation of the small magnetic body towards the arrhythmic substrate and the navigation of the liquid small magnetic body in small amounts as for the EPT in close proximity and conformal to the arrhythmic substrate cannot be simultaneous such as to prevent undesired EPT far away from the substrate and to assure stability at the arrhythmic substrate as well, during the EPT. Furthermore two separate navigation algorithms for a small magnetic body and for the liquid small magnetic body are needed. An adequate release flow rate of the EPT from the ink can through the internal lumen of the catheter device and mapping catheter is provided. A magnetic visualization of the magnetic staining ink in situ, conformal to the arrhythmic substrate may be provided in a dedicated magnetic field, time remote from the therapy as well.

To provide the electrophysiology therapy (EPT) to the arrhythmic substrate, the electrophysiology device, the catheter device (110) and the control unit (150) may be needed.

The catheter device preferably has a distal end and a proximal end. The distal end may be configured to be attached to a mapping catheter. A flexible shaft (140) connects the distal end and the proximal end. The flexible shaft can be made of a plastic material. The proximal end of the catheter device may be designed to be connectable to a handle for operating the functions and movements of the mapping catheter as well as the functions of the catheter device, the control unit or the sensor device.

The distal end of the catheter device comprises a plurality of electrodes, including tip electrodes, central electrodes according to the geometry of the mapping catheter that may be chosen to be linear, circular, basket, grid, mesh, orthogonal close unipolar or balloon among them. The electrodes of the catheter device can be located around the distal end with a predefined distribution and distance from one electrode to another. Each of the electrodes is connected via a plurality of low resistive wires to a plurality of connectors at the proximal end (130) of the catheter device. The proximal end of the catheter device may have a connecter for connecting the catheter device to a handle (180). The connector may comprise a screw-plug connection for establishing an electrical as well as a mechanical connection. A connection to the ink can is also provided.

The handle for operating the functions of the mapping catheter as well as the functions of the catheter device may have at least one operating element to control the control unit (150). The handle may have at least one electrical connection for connecting the handle to the control unit. Preferably, the electrical connection of the catheter device corresponds to electrical connection of the handle. In one embodiment, the handle can be located in the signal path between the catheter device and the control unit.

The sensor device is connected by the selector switch to at least one of the electrodes which can be the same or another than the electrode connected to the resistor. The configuration of the resistor according to the electrodes and the sensor device is dependent of the measurement task, which has to be executed. In one embodiment, the sensor device is configured to record the voltage and current over time. In other words, the sensor device is able to detect at which time which electrical potential is at a dedicated electrode. In another embodiment, the sensor device can be configured to measure the current channeled out of the heart by one of the electrodes. The catheter device may further comprise a control terminal with a display for controlling the measurement results as well as the chosen settings of the catheter device. The screen can be configured as a touch screen to control the functions of the catheter device or the control unit.

The neutral electrode may be connected to the at least one resistor or the sensor device directly or via at least one selector switch (not graphically displayed) which may be part of the control unit and may be configured to be attached to a patient. The neutral electrode closes the electrical circuit via the at least one electrode at the distal end of the catheter. For attaching the electrode to a patient, the neutral electrode may have an adhesive surface.

The flexible shaft may have several working channels as guide for several tools or electrical, optical or mechanical connections such as low resistive wires. The working channels can also be used as media feed-through for example for liquids. The catheter device may have a diameter from approximately 1 to 5, preferably from 1 to 3 mm.

The flexible shaft may include at least one wire, which can be formed of a super elastic material and can be shaped to bias the flexible shaft as well as the distal end in several orientations. The super elastic wire may be connected to a control element of the handle.

In a second embodiment of the invention, the cardiac electrophysiology device is configured to be an internal compound of a cardiac implantable device, such as a pacemaker (PM}, a defibrillator (ICD) or a contractility modulation (CCM) device. All these devices, except CCMs possess pacing functions that according to specific pacing algorithms provide a paced rhythm to the heart by sequentially pacing one or more heart chambers. By adding synchronized non excitatory potentials, CCMs optimize the mechanical response of a paced rhythm of the heart as provided by PMs and ICDs. In order to establish when, if and which pacing algorithm is activated, to create a paced rhythm of the heart, the cardiac implantable devices above mentioned possess sensing functions. The sensing functions, according to specific sensing algorithms can determine if the heart exhibits a spontaneous electrical activity or not, if yes, whichever it might be, if it involves or not an arrhythmia. When the spontaneous electrical activity of the heart is interpreted according to the sensing algorithms to indicate an arrhythmia, the detection specific algorithms are activated in order to characterize that arrhythmia.

The cardiac electrophysiology device may be configured to be an internal compound, optionally be part of the electrical circuitry of a cardiac implantable device (CID) as mentioned below or part of an implantable lead of a CID. The neutral electrode may be configured to be part of the housing of the cardiac implantable device or may be configured to be a floating electrode. The electrophysiology device may be optionally configured to receive input data when an arrhythmia is present, from both the sensing and detection algorithms as of a cardiac implantable device that further on, may be a cardiac pacemaker, defibrillator or a contractility modulation device.

Both sensing and detection algorithms of the cardiac implantable device (CID) below mentioned, provided that it incorporates the cardiac electrophysiology device disclosed herein by the invention as part of its electrical circuitry or part of an implantable lead, may be configured to receive inputs from the sensor device (160) and further on to define an arrhythmia whenever the inputted value from the sensor device represents a negative differential resistance (NOR}, as herein depicted below. The inputs may be configured to be the instantaneous measured values provided by the voltmeter (161) and the current meter (162). Preferably, these inputs include the value of instantaneous differential resistance as provided by the sensor device (160) as a result of computing the instantaneous values furnished by the voltmeter (161) and the current meter (162).

Furthermore, the cardiac implantable device (CID) above mentioned, provided that it incorporates the cardiac electrophysiology device as disclosed by the invention may be configured to set and to alter the setting of both the first (156) and the second (155) selector switches of the cardiac electrophysiology device according to a multipolar configuration of at least one of the implantable leads of the CID, which now herein disclosed by the invention. Both the unipolar and bipolar connecting modes of the sensor device (160) may apply, according to the previous description of the sensor device 160 refreshed herein below.

In whichever case and provided that the first selector and the second selector switch refer to the same selected electrode, the sensor device 160 may be said to work in an unipolar mode. Again, in whichever case and provided that the first and the second selector switch refer to different selected electrodes, the sensor device 160 may be said to work in a bipolar mode. Preferably, the value of the resistor is set high for the bipolar mode, or optionally low for the unipolar mode.

The electrophysiology device may be configured to connect the resistor to at least one of the at least two active electrodes, if an arrhythmia is detected according to the detection algorithms above mentioned or when, according to the invention, an arrhythmia is defined whenever the instantaneous value of the differential resistance provided from sensor device 160 is or turns negative. By setting the value of the variable resistor, current can be set up to be channeled out from the heart via at least one electrode at the distal end of the electrophysiology device. The amended current dissipation can be recorded via the sensor device 160 and may be configured to be maximal depending upon the setting of the value of the resistor (either a very low or a very high setting within, but not limited to the proposed ranges, from 0.10 ohm to 2 mega ohm).

Such therapies can be activated and delivered by CID through the electrophysiology device and the implantable leads as many times as the arrhythmia presents itself. That involves a repeatedly out-channeling of current out of the heart by setting and changing the setting of the resistor and of first and/or second selector switch until the arrhythmia terminates. The setting and the sequence in which the settings of the resistor and of first and/or second selector switches are changed to prevent the occurrence of an arrhythmia or during an arrhythmia until the arrhythmia terminates may be programmed as part of the conventional programming session of the CID, which disclosed herein above. They may be configured to provide in case of an arrhythmia the maximal current out-channeled out from the heart to terminate that arrhythmia. In further embodiments an innovative design is further needed for the implantable leads of the CID, beyond the frame, but without leaving the scope of this invention.

When the heart beats too slowly or does not exhibit a spontaneous electric activity at all, a so called bradycardia, the cardiac implantable devices like pacemakers or defibrillators provide programmable voltage outputs to the heart which result in electric stimuli that pace the heart to a normal frequency.

When the heart beats too rapidly as during a tachycardia, pacemakers can provide series of programmable voltage outputs, to overdrive that tachycardia, defibrillators can further on deliver electrical shocks to terminate the tachycardia if the previous overdriving algorithms proved to be ineffective. Cardiac contractility devices may temporarily inhibit all their pacing algorithms.

Both overdriving a tachycardia and the deliverance of an electrical shock in an intent to terminate such an arrhythmia are achieved by applying of some increasing external voltages to the heart. It involves a rightwards slippage of the arrhythmic substrate VI relationship along the NOR domain during an arrhythmia in an intent to diminish the current I up to a critical I minimum point 2 or 3 that actually interrupts the arrhythmia.

According to the invention, the rightwards slippage along the NDR domains is directly achieved by primarily decreasing current at the level of the arrhythmia substrate by channeling current out of the heart according to the innovative therapy proposed by the invention, until the arrhythmia terminates. This therapy has less negative impact and less side effects in comparison with the conventional therapies (overdrive burst, ramps and shocks}, which known from prior art typically provided by conventional cardiac implantable devices such as pacemakers and defibrillators.

According to the invention, the first and the second embodiments apply to clinical settings, involving both bradycardia and/or tachycardias and do not exclude each other. The decision to choose either one therapy or both, according to whichever of the two embodiments disclosed herein in the invention, is proposed as a joint decision of the patient and the physician.

FIG. 1 shows a catheter device 110 with a handle 180. The catheter 110 is divided into three parts. The catheter 110 has a proximal end 130 a flexible shaft 140 and a distal end 120.

The distal end has a plurality of electrodes 121, 122, 123, 124.

The handle 180 has two operating elements 181, 182 to control the function of the catheter or the catheter device. In this configuration, the handle 180 can be configured to control the distal end 120 of the catheter 110 via the operating element 181. The handle 180 can be further configured to trigger different measurement functions of the catheter device, respectively of the control unit or the sensor device via the operating elements 182. The handle 180 can have at least one electrical connection for connecting the handle to the catheter device 110 and a connection to the ink can.

Figure 2:
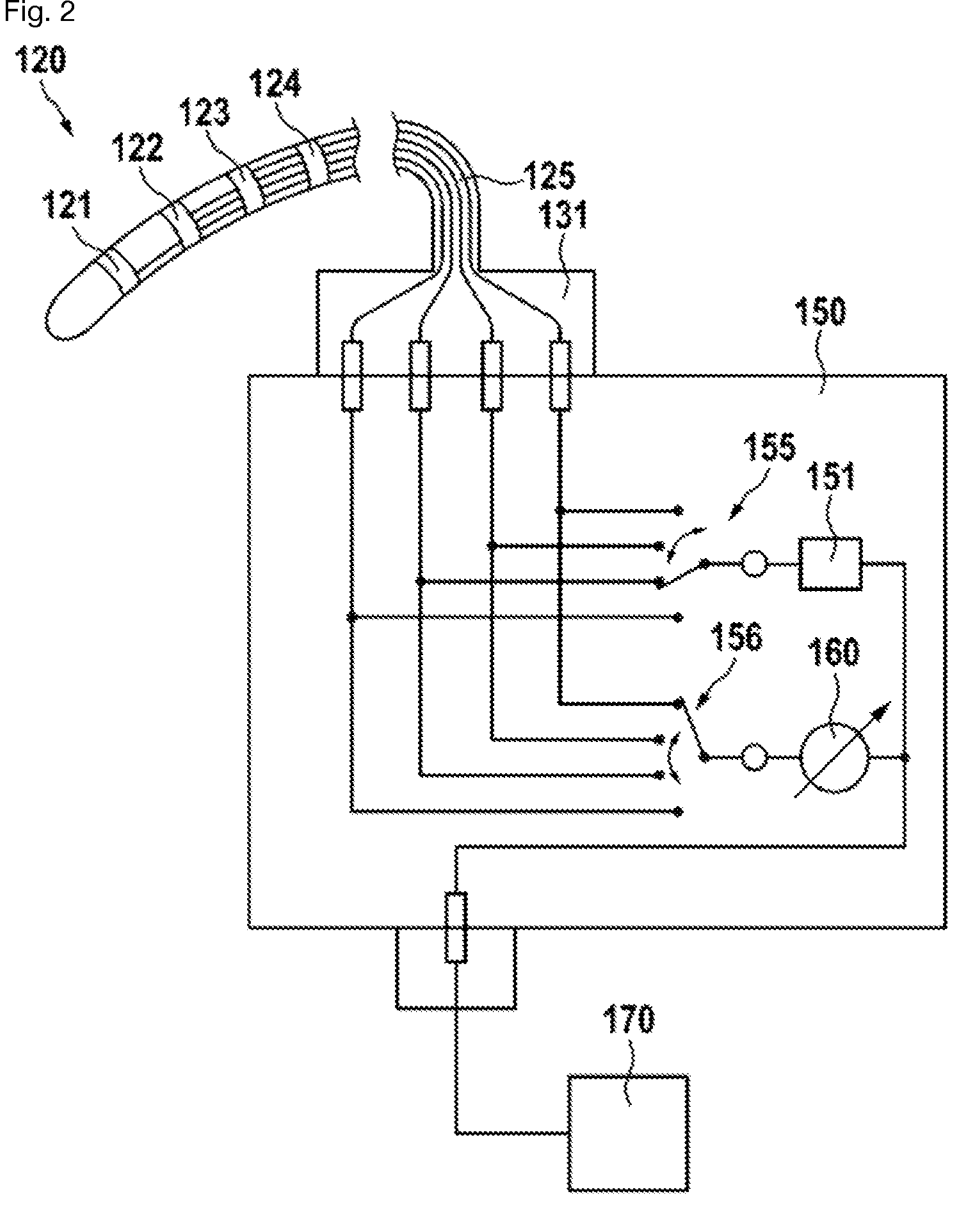
FIG. 2 shows a schematic diagram of the electrophysiology device-catheter device assembly.

FIG. 2 shows a schematic diagram of the electrophysiology device-catheter device assembly. It has at its distal end 120 a plurality of electrodes 121, 122, 123 and 124. Although here four electrodes are shown, the catheter device may have any number of electrodes between 2 and 20, preferably between 6 and 16 disposed on the mapping catheter, according to the specific geometry of the mapping catheter. These electrodes are connected via low resistive wires 125 in the catheter and a connector 131 to a control unit 150. The control unit comprises a second selector switch 155 connected to the electrodes and a resistor 151. It is not necessary that the selector switch is connected to all electrodes. Two electrodes or more are sufficient. The resistor may be a fixed or a variable resistor. It preferably is in the range from 0.10 to 2 mega ohm. The control unit comprises a first selector switch 156 connected to the electrodes and a sensor device 160. The sensor device may be a voltage or current meter. The term voltage or current meter includes all devices which are able to measure voltages and currents. This includes amplifiers and analog/digital converters which may provide digital information to a computer. It is not necessary that the selector switch is connected to all electrodes. Two electrodes or more may be sufficient.

A neutral electrode is connected to the resistor and/or sensor device.

This neutral electrode 170 allows current from the heart 200 of the patient to flow back to the body. For attaching the neutral electrode 170 to a patient, the neutral electrode 170 may have an adhesive surface.

Figure 3:
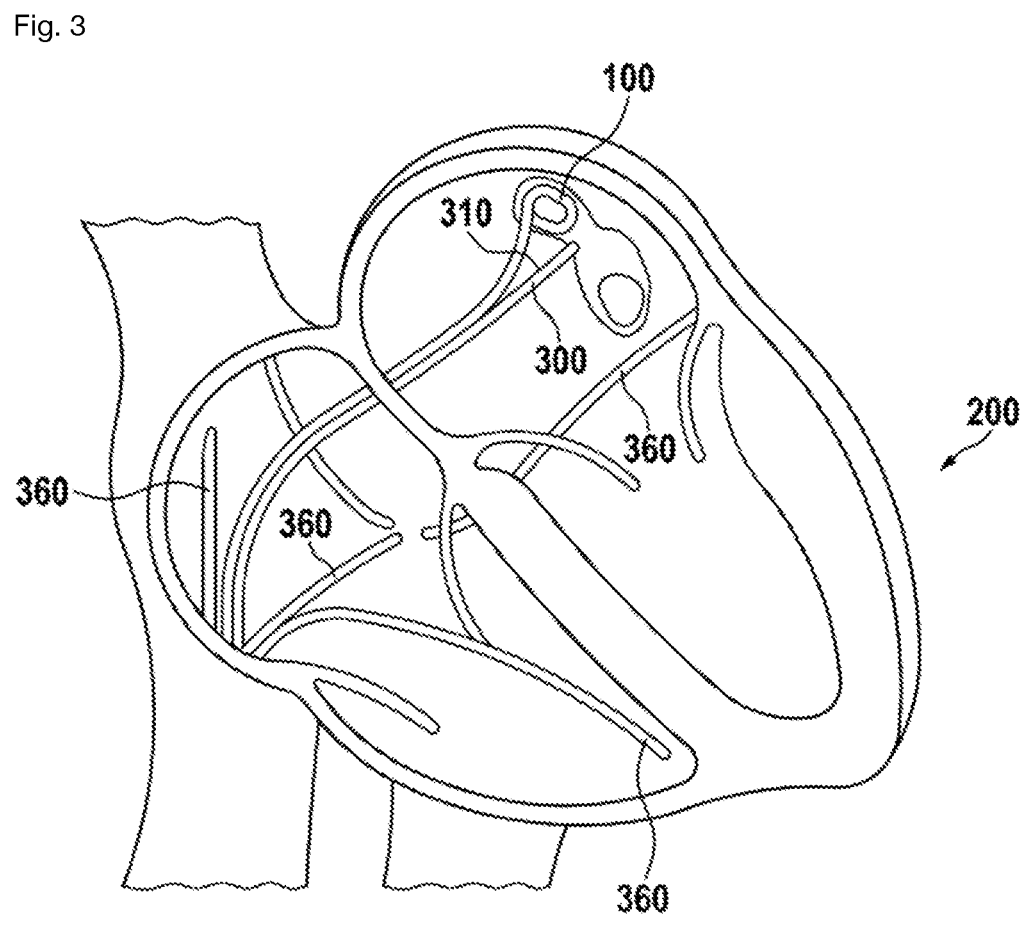

FIG. 3 shows a heart 200 in detail. An additional mapping catheter 360 can be used; the ink staining 300 of the arrhythmic substrate by a tip assembly 310 of the catheter is provided and displayed.

FIG. 4 shows the VI (voltage-current) electronic distribution at the level of the arrhythmic substrate. Both the N-shaped and the 5-shaped VI distributions are shown. An arrhythmia is present when the arrhythmic substrate has a NDR behavior and is absent whenever the arrhythmic substrate has a non-NDR behavior. Typically, an increasing voltage applied to the substrate triggers an arrhythmia at point 1 or 3, and terminates a given arrhythmia at point 2 and respectively 3 and, vice versa, a decreasing voltage applying to the substrate, triggers an arrhythmia at point 2 or 4 and further on terminates the given arrhythmia at point 1 or 4.

Although the invention has been illustrated and described in detail by the embodiments explained above, it is not limited to these embodiments. Other variations may be derived by the skilled person without leaving the scope of the attached claims.

In addition, numerical values may include the exact value as well as an usual tolerance interval, unless this is explicitly excluded.

Features shown in the embodiments, in particular in different embodiments, may be combined or substituted without leaving the scope of the invention.

LIST OF REFERENCE NUMERALS

110 catheter device
121 distal end
121-124 electrodes
125 low resistive wires
130 proximal end
131 connectors
140 flexible shaft
141 flexible wire
150 control unit
151 resistor
156 first selector switch
155 second selector switch
160 sensor device
161 voltage meter
162 current meter
170 neutral electrode
180 handle
181 operating element
182 operating element
200 heart
300 stained ink
310 tip assembly
360 additional mapping catheter Keywords electrophysiology therapy (EPT}, staining ink, conformal, magnetic, negative (differential) resistance, current channeling out, arrhythmic substrate cardiac mapping (mapping}, electronic mapping, three dimensional mapping, magnetic mapping electrophysiology device, catheter device, control unit electrophysiology procedure

The invention claimed is:

1. A cardiac electrophysiology device comprising:

at least one active electrode, a neutral electrode, a sensor device comprising voltage and current meters, the sensor device being connected to the neutral electrode, and being configured to measure an instantaneous voltage and current, and output of a value of an instantaneous differential resistance based on the instantaneous voltage and current;

a first selector switch connected to a first active electrode of the at least one active electrode and to the sensor device, the first selector switch being configured to electrically connect the sensor device to the first at least one active electrode;

a resistor having a value in a range from 0.10 ohm to 2 mega ohm, the resistor being electrically connected to the neutral electrode;

a second selector switch electrically connected to a second active electrode of the at least one active electrode and to the resistor, the second selector switch being configured to electrically connect the resistor to the second active electrode, wherein the cardiac electrophysiology device is part of a cardiac implantable device or of an implantable lead, wherein the cardiac implantable device is a cardiac pacemaker, a cardiac defibrillator or a contractility modulation device and wherein the neutral electrode is configured to be part of a housing of the cardiac implantable device or a floating electrode; and, a control unit is configured to receive input data from the sensor device, the input data comprising the value of the instantaneous differential resistance, and to define an arrhythmia or a predisposition to the arrhythmia when the value of the instantaneous differential resistance is negative, and being the control unit is further configured to interrupt the arrhythmia by channeling current out from the heart by varying the value of the resistor and first and/or second selector switch until the arrhythmia terminates, the varying being accomplished in either a unipolar or a bipolar mode to maximize a current dissipation recorded by the sensor device, wherein the interruption of the arrhythmia occurs by remote sensing of the arrhythmia.

2. A catheter device comprising the cardiac electrophysiology device of claim 1 and a mapping catheter.

3. The cardiac electrophysiology device of claim 1, wherein the cardiac electrophysiology device is configured to channel current out from the heart whenever a predisposition of an arrhythmia in the absence of an arrhythmia is defined.

4. The cardiac electrophysiology device of claim 2, wherein the mapping catheter is multipolar.

5. The cardiac electrophysiology device of claim 2, wherein the mapping catheter has an architecture selected from the group consisting of a linear architecture, a circular architecture, a grid architecture, a mesh architecture, an orthogonal close unipolar architecture, a basket architecture, and a balloon three dimensional architecture.

6. The cardiac electrophysiology device of claim 2, wherein the mapping catheter is an open irrigated catheter.

7. The cardiac electrophysiology device of claim 2, wherein the mapping catheter is configured to irrigate ink for ink staining.

8. The cardiac electrophysiology device of claim 2, wherein the catheter device comprises a distal end connected by a flexible shaft to a proximal end, the distal end comprising the at least one active electrode, each of the active electrodes being connected via a plurality of low resistive wires to at least one connector at the proximal end.

9. The cardiac electrophysiology device of claim 8, wherein the distal end comprises a plurality of active electrodes sufficient to cover a full extent of an arrhythmic substrate.

10. The cardiac electrophysiology device of claim 8, wherein the flexible shaft comprises at least one flexible wire formed of a superplastic material and shaped to bias the distal end in at least one orientation in response to the movement of an operating element of the catheter device.

11. The cardiac electrophysiology device of claim 2, wherein the catheter device comprises a handle configured to control the control unit, the handle comprising an operating element for triggering different measurement functions of the control unit or measurement of the sensor device.

12. The cardiac electrophysiology device of claim 1, wherein the neutral electrode is configured to be attached to a patient.

* * * * *